US010139636B2

(12) United States Patent
Lebrun et al.

(10) Patent No.: US 10,139,636 B2
(45) Date of Patent: Nov. 27, 2018

(54) METHODS FOR AUGMENTED REALITY

(71) Applicant: Essilor International, Charenton-le-Pont (FR)

(72) Inventors: Charles Lebrun, Charenton-le-Pont (FR); Konogan Baranton, Charenton-le-Pont (FR)

(73) Assignee: Essilor International, Charenton-le-Pont (FR)

(*) Notice: Subject to any disclaimer, the term of this patent is extended or adjusted under 35 U.S.C. 154(b) by 0 days.

(21) Appl. No.: 15/126,558

(22) PCT Filed: Feb. 23, 2015

(86) PCT No.: PCT/EP2015/053754
§ 371 (c)(1),
(2) Date: Sep. 15, 2016

(87) PCT Pub. No.: WO2015/139919
PCT Pub. Date: Sep. 24, 2015

(65) Prior Publication Data
US 2017/0090204 A1    Mar. 30, 2017

(30) Foreign Application Priority Data
Mar. 20, 2014   (PA) ..................... 14305397

(51) Int. Cl.
*G09G 5/00*    (2006.01)
*G02B 27/01*   (2006.01)
*A61B 3/09*    (2006.01)
*G06F 1/16*    (2006.01)

(52) U.S. Cl.
CPC ............ *G02B 27/0179* (2013.01); *A61B 3/09* (2013.01); *G02B 27/017* (2013.01); *G02B 27/0172* (2013.01); *G06F 1/163* (2013.01); *G06F 1/1637* (2013.01); *G02B 2027/0178* (2013.01); *G02B 2027/0181* (2013.01)

(58) Field of Classification Search
CPC .......... G02B 27/0172; G02B 2027/014; G02B 27/0179
See application file for complete search history.

(56) References Cited

U.S. PATENT DOCUMENTS

| 3,460,530 | A | 8/1969 | Lorenz |
| 6,048,064 | A * | 4/2000 | Hosoi ................. A61B 3/0025 351/212 |
| 7,857,444 | B2 | 12/2010 | Moliton et al. |
| 2003/0234823 | A1* | 12/2003 | Sato ....................... G06F 3/013 715/848 |
| 2010/0045927 | A1* | 2/2010 | Moliton ............. G02B 27/0103 351/158 |
| 2012/0019775 | A1* | 1/2012 | Tyrin ...................... A61H 5/00 351/203 |

FOREIGN PATENT DOCUMENTS

| EP | 0716329 A1 * | 6/1996 | .......... G02B 27/017 |
| EP | 0716329 B1 | 8/2003 | |
| WO | 2011076604 | 6/2011 | |

* cited by examiner

Primary Examiner — Nan-Ying Yang
(74) Attorney, Agent, or Firm — Oblon, McClelland, Maier & Neustadt, L.L.P.

(57) ABSTRACT

The invention relates to methods for augmented reality. The invention relates more particularly to methods for improving the visual comfort of a wearer equipped with a head-mounted display device.

17 Claims, 6 Drawing Sheets

METHODS FOR AUGMENTED REALITY

FIELD OF THE INVENTION

The invention relates to methods and systems for augmented reality.

The invention relates more particularly to methods for improving the visual comfort of a wearer equipped with a display head-mounted device, especially for situations wherein the wearer visualizes both a 'real' display from the wearer environment and a 'virtual' display of computer-generated content displayed by the head-mounted device.

BACKGROUND OF THE INVENTION

Head-mounted display devices (HMDs) are known in the art. Such devices include so-called 'smart glasses', which allow the wearer thereof to visualize information content such as images or text for augmented reality.

When wearing such head-mounted device, the wearer may find himself/herself in situations of 'dual' visualization. Namely, the wearer may wish to look at a 'real' object from the environment (for example, a monument or a traffic sign) and at a virtual display provided/generated by the HMD (for example, information about the monument or driving directions). Thus, the wearer should be able to switch rapidly and comfortably between the visualization of the 'real' world (environment of the wearer) and the visualization of the 'virtual' display provided by the HMD. Therefore, the HMD should be designed in such a way that minimal accommodation efforts are required for the wearer in such situation.

EP0716329A1 discloses a HMD wherein the display system can be adjusted so as to set the visualization distance of the virtual image. The proximity of the virtual display and that of the 'real' display are always the same. This system is inconvenient for the wearer, since it requires constant adjustment. Further, it lacks flexibility in that it does not contemplate situations wherein the 'distance' to the virtual display differs from that of the 'real' object visualized by the wearer.

According to the invention, the HMD can be optimized so that the wearer can comfortably switch from a 'real' visualization (that can be one or more objects in one or more of the following vision fields: far vision, near vision, intermediate vision) to a 'virtual' visualization (that can be at a set/fixed virtual distance of visualization, which occurs for example if the HMD comprises a LOE; or not set/fixed, as is the case for adjustable/settable systems) and vice-versa. Further, according to the present invention, the display HMD may be customized to the wearer.

SUMMARY OF THE INVENTION

In broad terms, the present invention relies on a step of assessing the wearer's dynamic accommodative facility.

The present invention generally provides:
methods for determining a virtual distance of visualization of information content displayed by a HMD,
methods for determining a virtual accommodation for visualization of information content displayed with a HMD,
methods for designing and/or manufacturing a HMD,
related computer program products and readable media, and
uses of a step of assessing a wearer's dynamic accommodation facility in a method of designing, manufacturing and/or setting a HMD.

Method for Determining a Virtual Visualization Distance

According to one aspect, the present invention provides a method for determining a virtual distance of visualization of information content displayed by a HMD.

The present invention provides a method for the determination of the value ($D\_v$) of a virtual distance of visualization by a wearer of computer-generated information content displayed by a head-mounted display device, wherein said method comprises a step of assessing the wearer's dynamic accommodative facility.

In some embodiments, said method comprises the steps of:
(i) Determining a value of comfort amplitude of accommodation ($Acc\_c$) of the wearer,
(ii) Assessing the wearer's accommodative facility under dynamic test conditions, by switching between the visualization of a first display and the visualization of a second display, wherein the second display is situated within the wearer's comfort amplitude of accommodation ($Acc\_c$), and
(iii) Determining a suitable value ($D\_v$) of virtual distance based on the results of (i) and (ii).

In some embodiments, step (ii) comprises the steps of:
(ii-a) Setting a first value ($d\_1$) of visualization distance of the first display,
(ii-b) Setting a second value ($d\_2$) of visualization distance of the second display situated within the wearer's comfort amplitude of accommodation ($Acc\_c$), and
(ii-c) Assessing the wearer's ability to accommodate during switching between:
the visualization of the first display situated at distance ($d\_1$), and
the visualization of the second display situated at distance ($d\_2$).

In some embodiments, step (ii) is designed to simulate the situation of the wearer switching between the visualization of a virtual display of information content displayed by said head-mounted display device and the visualization of a real object from the wearer environment. For example the values ($d\_1$), ($d\_2$) can be selected so as to simulate said situation.

In some embodiments, the method comprises:
repeating step (i) and step (ii), or
repeating step (ii), or
repeating step (i) and steps (ii-a) to (ii-c), or
repeating steps (ii-a) to (ii-c);
In some embodiments, steps (u-a) to (u-c) can be repeated, for example with a decreased gap value between ($d\_1$) and ($d\_2$).

In some embodiments, step (ii), respectively step (ii-c), comprises:
a qualitative assessment from the wearer, or
a quantitative assessment comprising one or more measurements, for example cyclic measurements.

In some embodiments, step (ii), respectively step (ii-c), comprises an accommodative rock test with lens flippers.

In some embodiments, step (i) comprises:
computing a value of comfort amplitude of accommodation ($Acc\_c$) based upon the age of the wearer, or
performing one or more measurements, for example according to the Push-Up method or according to a test with an active lens or objective measurement.

Method for Determining a "Virtual" Accommodation: Accommodation for the Visualization of a Virtual Target According to another aspect, the invention provides methods for determining a virtual accommodation for visualization of information content displayed with a HMD.

The present invention provides a method for the determination of a virtual amplitude of accommodation (Acc_v) for the visualization by a wearer of computer-generated information content displayed by a head-mounted display device, comprising a method for the determination of a value (D_v) of virtual distance of visualization as described herein.

Method for Designing a HMD

According to another aspect, the present invention provides a method for designing a HMD with display features.

The present invention provides a method for the design of a head-mounted display device intended to be worn by a wearer, wherein the device is capable of displaying computer-generated information content, comprising:
  the method for the determination of the value (D_v) of a virtual distance as described herein, or
  the method for the determination of a virtual amplitude of accommodation (Acc_v) as described herein.

In some embodiment, the device is a pair of glasses comprising two ophthalmic lenses and one of said ophthalmic lenses comprises a light-guide optical element.

In some embodiments, the method for the determination of the value (D_v) of a virtual distance (respectively the method for the determination of a virtual amplitude of accommodation (Acc_v)) is performed at least twice, with different gaze directions for the visualization of the first display and/or with different gaze directions for the visualization of the second display.

In some embodiments, the lenses are selected from prescription lenses, such as single-vision lenses, multi-focal lenses and progressive lenses, and the value D_v or Acc_v is used to determine one or more optical parameters of the ophthalmic lenses, such as the value of the base, the design of the front side or the design of the rear side of the lens.

Method for Manufacturing a HMD

According to another aspect, the present invention provides a method for the manufacture of a head-mounted display device intended to be worn by a wearer, wherein the device is capable of displaying computer-generated information content, comprising:
  the method for the determination of the value (D_v) of a virtual distance as described herein, or
  the method for the determination of a virtual amplitude of accommodation (Acc_v) as described herein, or
  the method for the design of a head-mounted display device as described herein.

Related Computer Programs Products

According to another aspect, the present invention provides computer program products and computer readable media that cause to perform any one of the methods as described herein.

In some embodiments, the present invention provides a method as described herein, wherein the method is computer-implemented.

In some embodiments, the present invention provides a (non-transitory) computer program product comprising one or more stored sequence(s) of instructions that is accessible to a processor and which, when executed by the processor, causes the processor to carry out the steps of any one of the methods as described herein.

In some embodiments, the present invention provides a (non-transitory) computer readable medium carrying out one or more sequences of instructions of said computer program product.

Uses

According to another aspect, the present invention provides a use of a step of assessing a wearer's dynamic accommodative facility in a method for designing, manufacturing or setting a head-mounted display device.

DETAILED DESCRIPTION OF THE INVENTION

Accommodation

The phenomenon of accommodation is known in the art. Irrespective of the age or of the possible ametropia of the wearer, the present invention provides for the determination (definition) of a space in the real-vision zone, wherein the visualization by the wearer of a real object and/or virtual object/display can be performed comfortably, namely with a restricted accommodation that is sufficient and non-spasmodic. The skilled person has common knowledge regarding the definition of accommodation, amplitude of accommodation, and how visualization distances are analyzed in this context.

Head-Mounted Display Device

Head-mounted display devices (HMD) are known in the art. Such devices are to be worn on or about the head of a wearer, including helmet-mounted displays, optical head-mounted displays, head-worn displays and the like. They include optical means for displaying (computer-generated) information content for visualization by the wearer. The HMD can provide for the display of computer-generated information content, advantageously with the superimposed visualization of computer-generated information content and of a 'real-life' vision field. The HMD may be monocular (single eye) or binocular (both eyes). The HMD of the invention can take various forms, including spectacles, masks such as skiing or diving masks, goggles, etc. The HMD may comprise one or more lenses. Said lenses can be selected from prescription lenses.

Figure 1:
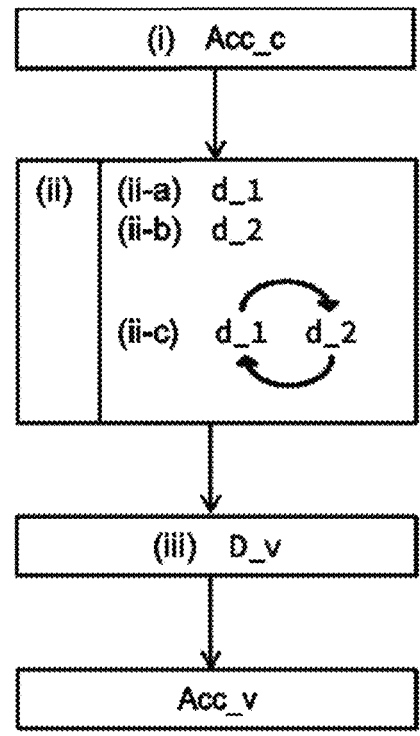
FIG. 1 shows an illustrative flowchart of the methods of the invention.
Figure 2:
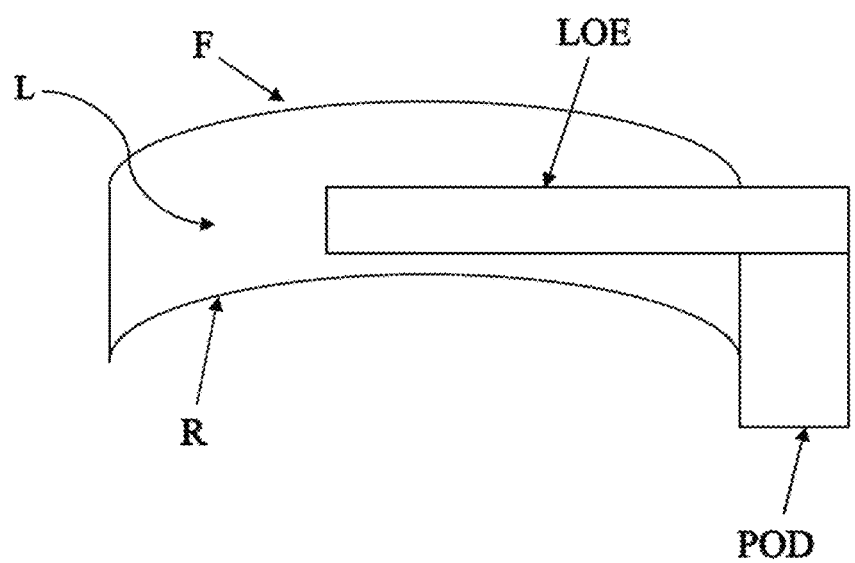
FIG. 2 shows a schematic representation of part of an illustrative HMD.

In preferred embodiments, the HMD is a pair of spectacles provided with lenses, wherein one or both of the lenses comprise a Light-guide Optical Element LOE. The HMD generally comprises a pod. Said pod can be a housing that contains optical and electronic components capable, in conjunction with the LOE, of generating (providing) a virtual display. An example of a lens L comprising a LOE is shown at FIG. 2. The lens L has a front face F facing the 'real world' (environment of the wearer) and a rear face R facing the wearer. The LOE is embedded within the lens L. The pod POD is connected to the LOE.

Figure 3:
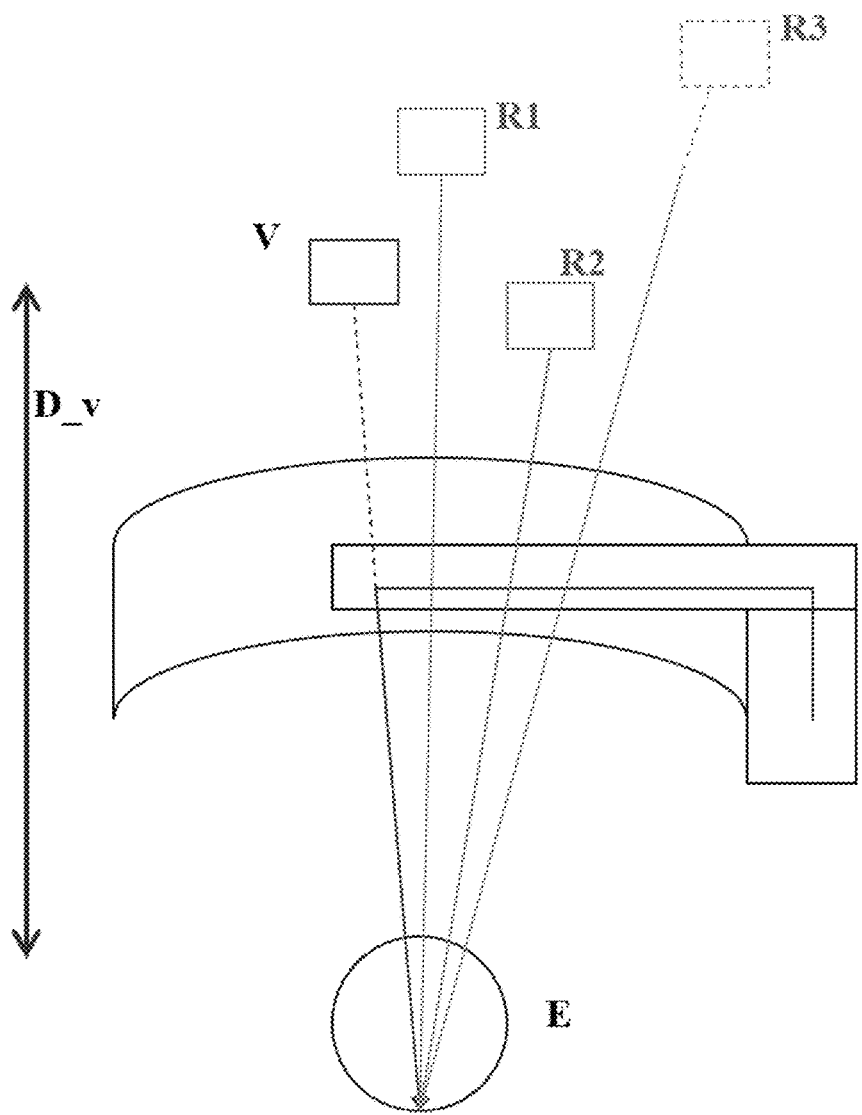
FIG. 3 shows a schematic representation of the visualization situation of a wearer equipped with a HMD.

The visual field of a wearer equipped with a HMD is depicted at FIG. 3. It shows that the wearer can be in a situation where s/he is to visualize a virtual display V provided by the HMD and 'real' objects from the environment R1, R2, R3. The virtual display is 'located' at a visualization distance D_v.

In general terms, for a virtual display, the light path for visualization is POD→LOE→Rear face of lens→Eye of wearer, whereas for a 'real' display (real object), the path is Object→Front face of lens→Rear face of lens→Eye of the wearer.

Determining Suitable Values of Virtual Distance of Visualization with a HMD

The present invention provides methods for determining suitable values of D_v, by taking into account the wearer's dynamic accommodative facility. The present invention thus provide methods for determining ranges of distances for the display of a computer-generated information content by the HMD, within which the wearer may comfortably visualize the display provided by the HMD, keep visualizing the 'real-world' including objects situated in the far-vision, intermediate and near-vision fields, as well as comfortably switching between the virtual display and the visualizing of the 'real-world', without incurring undue visual fatigue, thus experiencing high levels of visual comfort.

The invention relies on the following:
determining a value of comfort amplitude of accommodation (Acc_c) of the wearer,
assessing the wearer's accommodative facility under dynamic conditions, for example between a virtual display and a real display,
based on the above, determining a suitable range of distances for virtual displays.

In other terms, the invention relies on the following:
determining a value of comfort accommodation of the wearer (Acc_c) so as to deduce an accommodation value linked to a virtual display (Acc_v),
assessing the capacity of the wearer to switch from this virtual accommodation (Acc_v, corresponding to a virtual visualization distance) to a second accommodation value linked to a real display (Acc_r, corresponding to a real visualization distance) through the HMD,
depending on the switching capacity of the wearer, validate the value Acc_v (corresponding to virtual distance) or else change the value for Acc_v_bis (corresponding to another value of virtual distance) so as to reduce the gap between Acc_v_bis and Acc_r.

Determining the Comfort Amplitude of Accommodation of Wearer

Any method for determining the comfort amplitude of accommodation as known in the art can be used for the purpose of the present invention. This can result from a computation (estimation) or an actual measurement (ex: push-up method). Suitable methods for step (i) include modeling as a function of the age of the wearer, measurement with an optometric test and/or measuring with a device. Examples are given thereafter.

Assessing Dynamic Accommodation Facility of the Wearer

In general terms, in some embodiments, the invention involves a step of assessing the ability of a wearer to switch visualization between at least two visual targets. This corresponds to step (ii) as recited above. Said visual targets (e.g. displays) can be respectively visualized at respective distances d_1 and d_2, as recited above. The values of d_1 and d_2 can be selected so as to mimic (simulate) the situation of a wearer switching between the visualization of a virtual display (e.g., d_1) and that of a real object (e.g., d_2). In accordance with the invention, the first display and the second display may or may not be in the same gaze direction. The gaze direction can be defined as known in the art. Further, in accordance with the invention, the wearer's dynamic accommodative facility may be assessed by switching visualization between three or more displays 1, 2, 3 . . . . In such case, distances d_1, d_2 and d_3 can be set at same or different values, and/or in the same or different gaze directions. The visualization switch can for example be performed as follows: 1, 2, 3, 2, 1 . . . .

Figure 5:
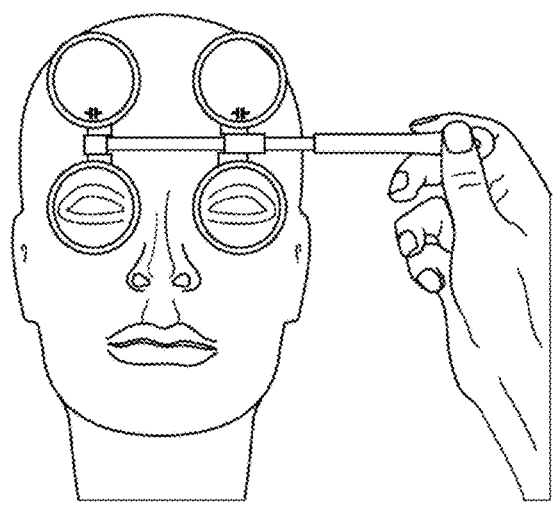
FIG. 5 shows an example of a lens flipper that can be useful according to the present invention.
Figure 6:
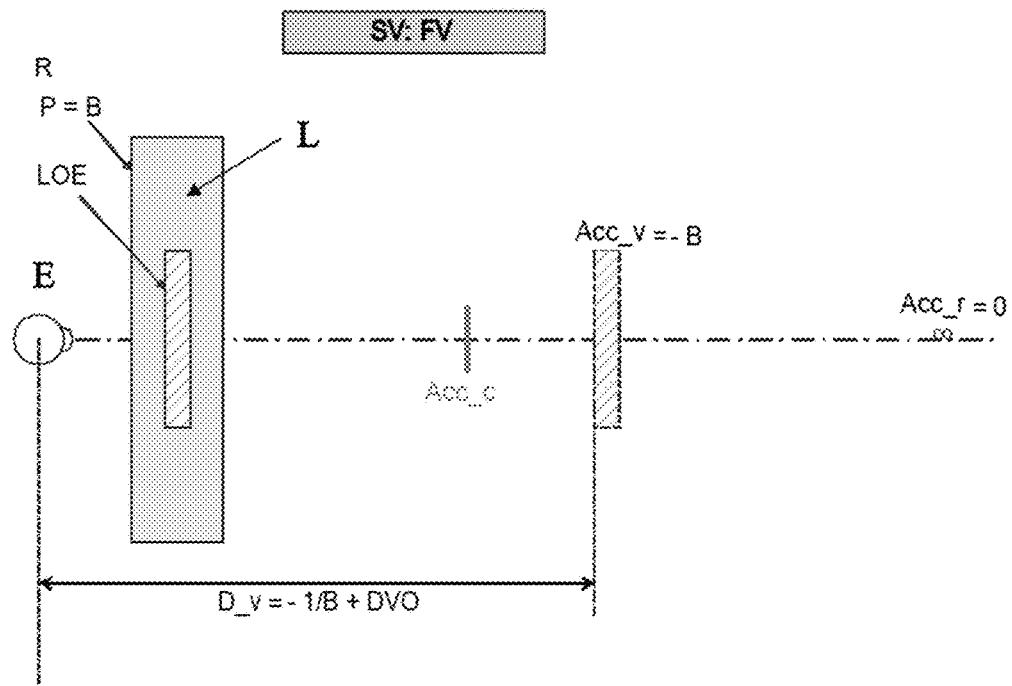
FIGS. 6-10 show graphic representation of various visualization situations of a wearer equipped with a HMD, wherein the HMD comprises a prescription lens.
Figure 7:
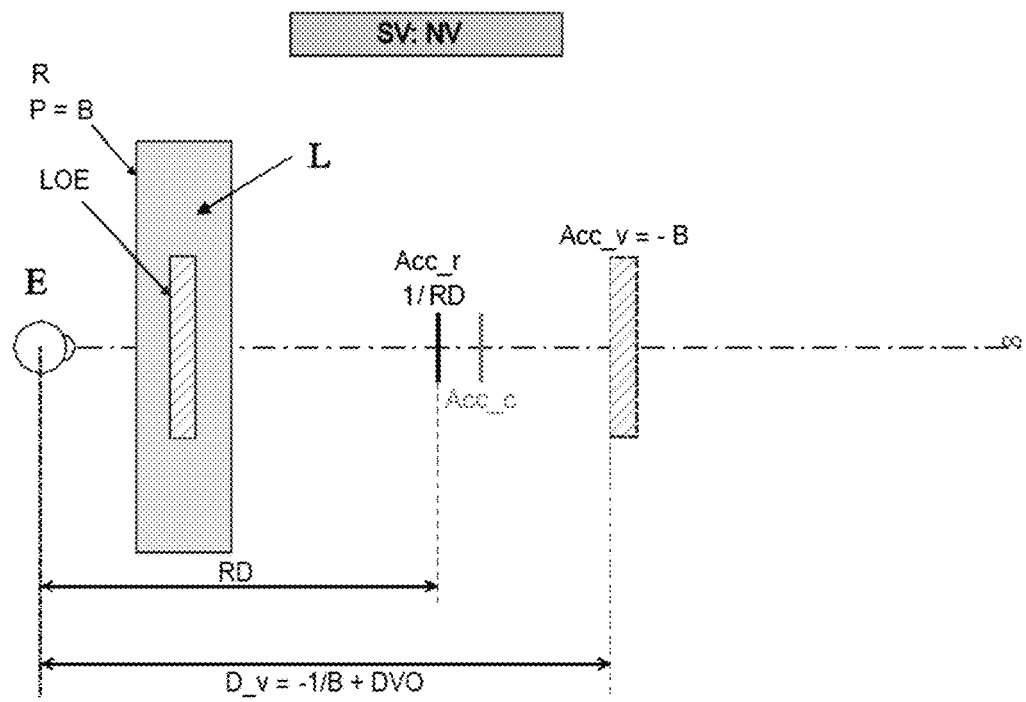
Figure 8:
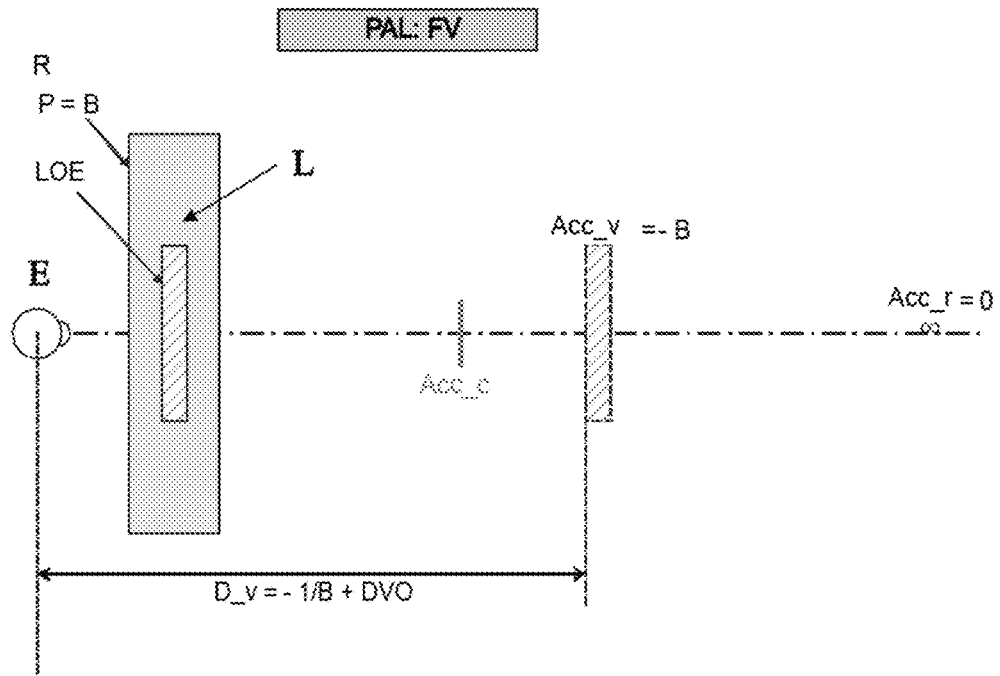
Figure 9:
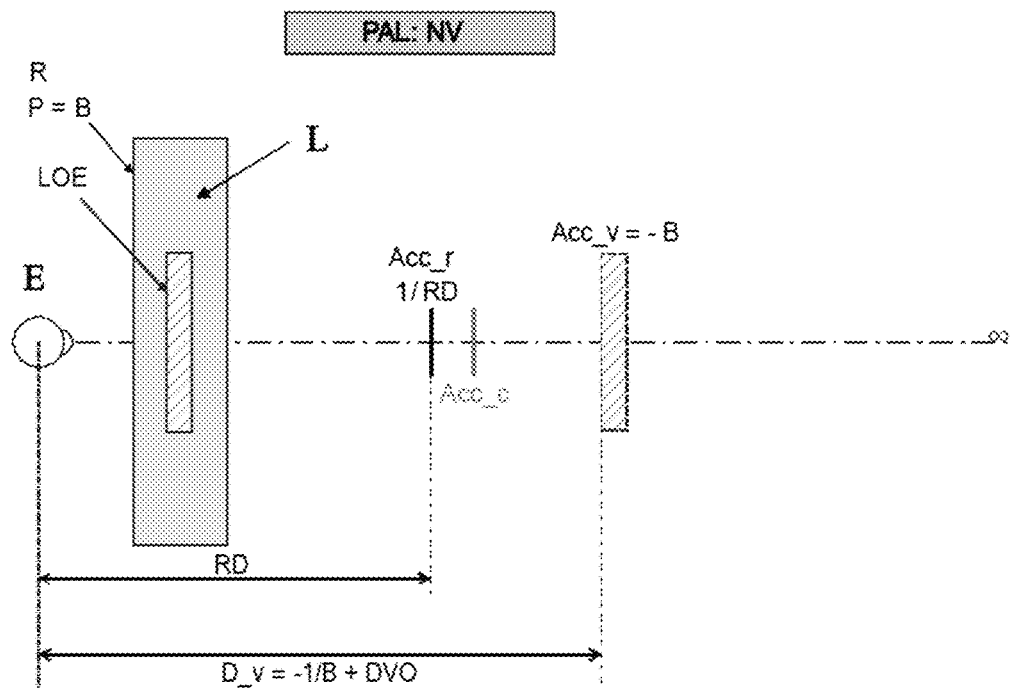

The assessment of the wearer's accommodative facility under dynamic test conditions can be performed on a qualitative and/or quantitative basis; on an objective and/or subjective basis, for example by using a proxymeter. An example of proxymeter is described at http://www.varilux-university.org/FR/Pages/Proxim%C3%A8tre.aspx. Step (ii) may be performed with one or more devices, or through an optometric measurement. Further, step (ii) may be performed with one or more pair of spectacles, including one or more smart glasses and/or one or more lens flippers. An example of a lens flipper is shown at FIG. 5.

The invention is illustrated by the following non-limiting examples.

EXAMPLES

Example 1: Determining Comfort Amplitude of Accommodation of Wearer: Determining Acc_c as Per Step (i)

Measurements related to comfort accommodation take into account the depth of field.

Measurements can allow access to the following quantities:
Punctum remotum (PR, furthest visible point, which is translated into diopters D), which corresponds to an accommodation of zero;
Punctum proximum (PP, closest visible point, translated into D), which corresponds to the maximal accommodation Acc_max;
Comfort accommodation can be defined as Acc_c=(⅔) Acc_max;
« Tonic accommodation» (value in D situated between PR and PP, also called resting accommodation).

These quantities vary from one wearer to another, but are also a function of age. Age can be regarded as a relevant factor for the determination of step (i). The below examples illustrate various methods for the determination of Acc_c.

Irrespective of the method used for determining Acc_c, it is preferred that Acc_v≤Acc_c.

Example 1.1: Model for the Computation of Acc_c as a Function of Age

Reference is made to FR2903503A1 and U.S. Pat. No. 7,857,444B2, the contents of which are incorporated herein by reference.

For an emmetrope eye, the visualization distance for which no effort is required is of 1 m. The maximal amplitude of accommodation decreases with the age of the subject. The comfort amount of accommodation (that can be 'implemented' without undue strain for the subject) is about ⅔ of the maximal amplitude. Thus the 'effortless' (fatigue-less) value of accommodation that may be used by the subject, decreases along with age.

|  | Age (yrs) | | | |
|---|---|---|---|---|
|  | 40 | 45 | 50 | 60 |
| Acc_max (D)* | 5 | 3 | 1.5 | 1 |
| Acc_c (D) | 3 | 2 | 0.5 | 0.25** |

*This maximum amplitude of comfort accommodation is established for near-vision by using the apparent proximity factor. This amplitude is less for a virtual display or for focusing on the far-vision zone for a non-corrected hypermetrope subject.
**At around the age of 60, this amplitude rather results from the depth of field (can typically be about 1D).

Example 1.2: Model for the Computation of Acc_c as a Function of Age, Taking into Account Tonic Accommodation This model incorporates the tonic evolution as a function of age. This advantageously provides for a more accurate estimate.

Values of accommodation (D):

|  |  | Age (yr) | | | | |
|---|---|---|---|---|---|---|
|  |  | 40 | 45 | 50 | 55 | 60 |
| Punctum Remotum | PR | 0 | 0 | 0 | 0 | 0 |
| Tonic accomm | TA | 1 | 0.67 | 0.16 | 0.12 | 0.083 |
| Punctum proxi comfort | PPc | 3 | 2 | 0.5 | 0.3 | 0.25 |
| Punctum proximum | PP | 5 | 3 | 1.5 | 1.2 | 1 |

Figure 4:
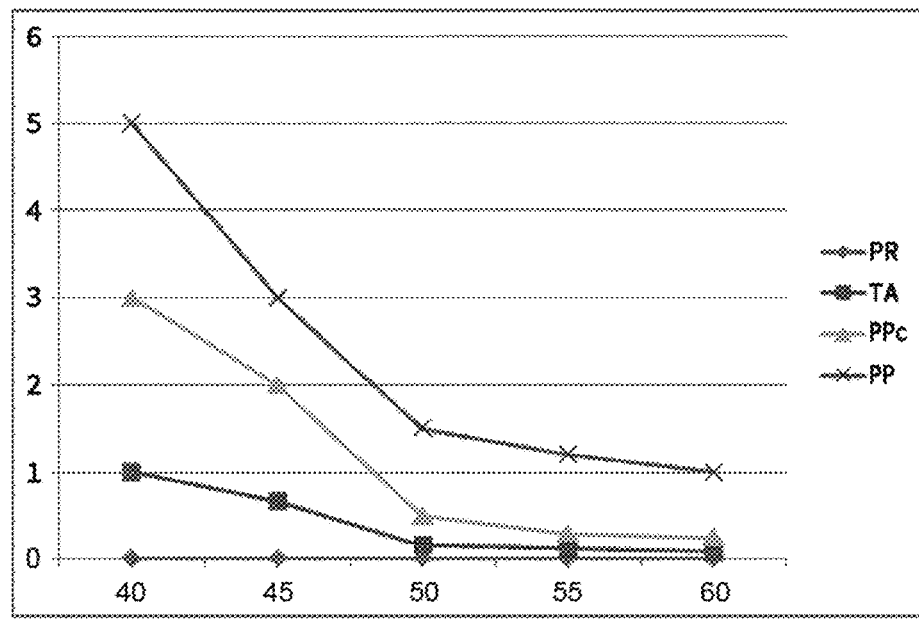
FIG. 4 shows a graphic representation of a model for determining the residual accommodation of a subject.

These values are shown on FIG. 4. The vertical axis represents Accommodation (D), while the horizontal axis shows age (Years). It illustrates the model for residual accommodation as a function of age.

For an ametrope wearer, the same values can be used, it suffices to use the same values and to deduct the prescribed value to obtain the values to be used.

Following examples 1.3 and 1.4 illustrate the determination of the comfort amplitude of accommodation Acc_c using first a determination of the maximal amplitude of accommodation Acc_max. In such case, one can determine Acc_c as two-thirds of Acc_max: $Acc\_c=(2/3)*Acc\_max$.

Example 1.3: Determination of Acc_c by Computing Maximal Amplitude of Accommodation This determination relies on a model for the computation of the maximum amplitude of accommodation as a function of the age of the subject. It can be determined using one of the models as follows (accommodation value in diopters, age in years):

model n°1 (higher values) Acc_max=25−0.40 age
model n°2 (average values) Acc_max=18.5−0.30 age
model n°3 (lower values) Acc_max=15−0.25 age
Example: for a subject who is 50-years old, using model n°3: Acc_max=2.5
$Acc\_c=(2/3)*Acc\_max=1.67$
P_c=60 cm: a display located at 60 cm or more from the wearer will always be comfortably visualized.

Example 1.4: Determination of Acc_c Using the Push-Up Method (PPA Method)

The Push-Up method is advantageous in that it is simple, quick, personalized and requires few instruments.

0.80 BCVA (80% best corrected visual acuity, i.e. of the best acuity obtained with the best correction): in the test, the visual target is selected so as lead to 80% of the best acuity,
Optimal compensation of the refraction,
A metered (e.g. millimeters) ruler, on which the dioptric equivalencies can be marked for the proximities and the minimal amplitudes as a function of age.
Natural Conditions:
Use of the trial frame,
This test advantageously takes into account the depth of field of the subject,
The measurements can be performed on a monocular or binocular basis.
Methodology:
The attention of the subject is drawn to the visual target (for example, a printed text) and the subject is asked to maintain focus as long and as precisely as possible.
The left eye is hidden and the measurement can start for the right eye.
The target is slowly and progressively brought closer, for example at about 0.25 to 0.50 δ per second in order to create a regular change in the accommodative response. The closer the target, the more slowly it should be brought closer, so as to keep a constant progression in diopters.
Stop as soon as the subject perceives a first constant blur and note the distance,
The process is to be repeated 3 times to obtain an average and observe the quality of accommodation.
Repeat for left eye and both eyes.
Alternatively, the test may be first conducted for binocular vision, and then for monocular vision of one or both eyes of the subject.
Example: The test provides a measured distance=>Acc_max.
$Acc\_c=2/3 Acc\_max$; $P\_c=1/Acc\_c$.
This enables to check that the comfort proximity (defined by the base curve of the lens, i.e. by the power of the rear face) of the wearer is equal or less than the display distance of the virtual display.

Example 2: Assessing Accommodative Facility of Wearer Under Dynamic Test Conditions, as Per Step (ii), Using an Accommodative Rock Test This example illustrates a method for the assessment of the wearer's capability to switch visualization of a virtual display (within virtual amplitude of accommodation, Acc_v) and visualization of another (real) display situated within a comfortable vision field of real visual targets.

This test is an accommodative rock test. It makes use of lens flippers, an example of which is represented at FIG. 5. The side thereof can be + or −2.00 D. The lenses are flipped (rotated) on a cyclic basis to switch from one pair of lens to the other.

The parameters of the test can be as follows:
RD: reading distance,
0.80 BCVA (80% best corrected visual acuity, i.e. of the best acuity obtained with the best correction),
Minimum number of rotations (cycles) to be performed (reached) per time unit (min),
Average number of rotations (cycles) to be performed per time unit (avg),
The test can be performed on a monocular or binocular basis.

The test generally allows to assess the rapidity and the resistance to fatigue of the ciliary muscle, of the crystalline lens, and/or the appropriate functioning of the efferent neurons involved in the accommodation process.

The test may be performed with various sphere values, so as to simulate the various distances (accommodation situations) that the wearer is likely to face. The test may be performed with a pair of smart glasses, or even with a set of several smart glasses.

The values of number of rotations per time unit (Min, Avg) can be determined by the skilled person as a function of the nature of the equipment used.

Illustrative example of accommodative rock test on a monocular (amblyope) or binocular basis:
0,8xBCVA,
Min: 12 cpm (cpm: cycle per minute)
Avg: 17 cpm.

More generally, besides possible quantitative determinations, the eye care specialist may perform a qualitative assessment of the visual behavior of the subject with respect to dynamic accommodation.

Example 3: Assessing Accommodative Facility of Wearer Under Dynamic Test Conditions, as Per Step (ii), for Different Types of Prescription Lenses In this example, it is assumed that the wearer's ametropia is corrected. The lenses are prescription lenses having a LOE embedded therein, for example as per FIG. 2. FIGS. 6-9 show visualization situations with different ophthalmic lenses.

The legend of the figures is as follows:
SV: single vision lens; PAL: progressive addition lens,
NV: near vision; FV: far vision,
L: lens; E: eye,
B: lens base curve; P: power,
LOE: light-guide optical element,
RD: reading distance,
Acc_c: comfort accommodation,
Acc_r: real accommodation (visualization of real display),
Acc_v: virtual accommodation (visualization of virtual (HMD-generated) display),
Box delimited with dash-lines and filled with hatched lines: virtual object, HMD-generated information content display, corresponding to the projection by the HMD POD through the LOE after conjugation through the rear face of the lens
DVO: distance between the eye and the lens (back vertex distance),
D_v: virtual distance, distance of display of virtual information content.

On the figures, the value for comfort accommodation Acc_c is located in an informal manner, and it could be set and placed equal to the accommodation involved at the reading distance. The value of real accommodation Acc_r depends on the reading distance RD, in average of 40 cm.

For non-presbyopic ametropic wearer, one should check that the wearer is capable, from a virtual value of accommodation Acc_v (defined by the lens base), to:
Mobilize additional accommodation required for clear and comfortable vision at the reading distance,
Relax the virtual accommodation Acc_v for a clear and comfortable vision (in far vision for example).

For presbyopic wearers, one should check that the wearer is capable, from a virtual value of accommodation Acc_v, to relax this residual accommodation or depth of field, for a clear and comfortable vision at the reading distance and in far vision.

When performing step (ii), the dioptric modulation cycles allow to assess the capability of the subject to switch from visualizing a virtual display (e.g. at distance D_v or d_1) to a real display (e.g. at distance d_2 corresponding to Acc_r, for example within Acc_c, in NV or FV zones), with vergences included.

The virtual display can be projected in various locations (gaze directions) of the visual field, as a function of the location of the LOE within the lens. The wearer may thus be in one of the following situations:
The virtual display is located in the upper part of the lens (far vision),
The virtual display is located in the lower part of the lens (near vision),
The virtual display is located in a part of the lens that is not used much by the wearer.

In some situations, the wearer can visualize a real scene (real objects) through the virtual display. In that situation or if the virtual display is located in another part of the lens, the accommodation values to be implemented when switching from one to the other are very close. The same test principle can then be used.

Figure 10:
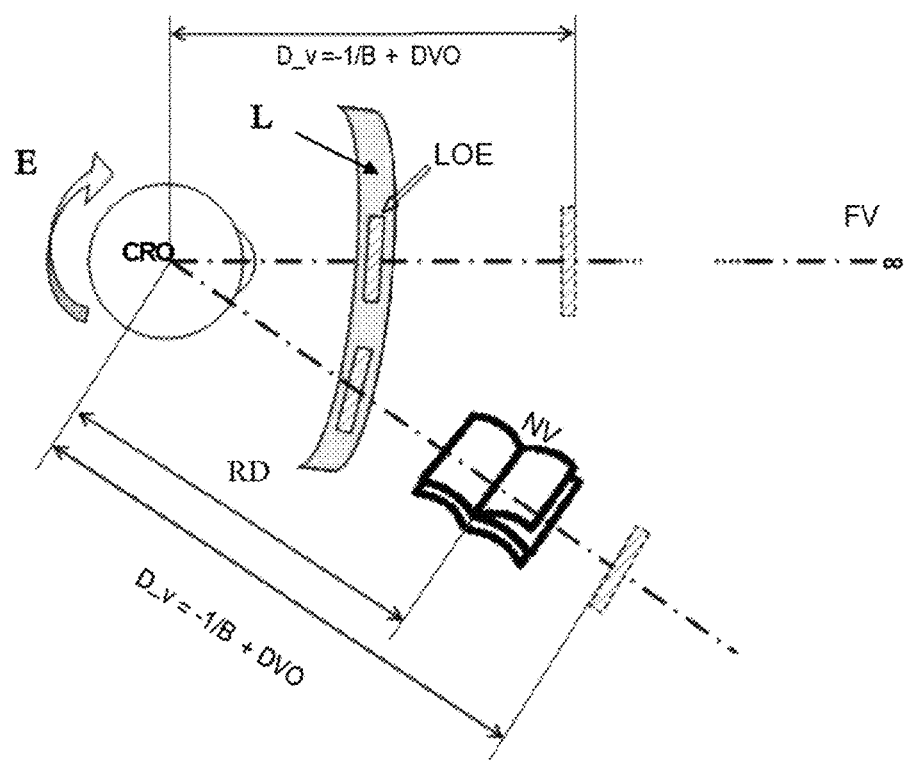

Distance D_v can be determined by taking into account different gaze directions, as illustrated at FIG. 10. Legend is as before, and CRO=center of rotation of the eye.

Example 4: Method Validation and Determination of D_v Range Values

If the accommodative rock test (or other assessment of step (ii)) is successful (for example, sufficient number of cycles per minute), and/or if the wearer does not complain about fatigue or discomfort or pulling sensation, then a device (LOE+POD) can be designed so as display (project) the virtual display at a distance that should be comfortable and suitable for the wearer. The value Acc_v (or value D_v) is set for designing and manufacturing the HMD.

If the accommodative rock test (or other assessment of step (ii)) is not successful, then the value Acc_v (or value of D_v or d_1) can be altered so as to reduce the gap between d_1 and d_2 (Acc_v and Acc_r). It is then possible to modify the base curve of the lens that contains the LOE. The virtual display will then be displayed at a farther distance (after conjugation with the rear face) and the accommodation required for a clear and comfortable vision will be decreased.

By way of example:
Subject is 48 years-old. Acc_max=3 D, so that Acc_c=2 D (50 cm).
Lens has a base curve of 2; so that Acc_v=1.90 D: rock between the infinite (far vision) and 53 cm. If not OK, the lens can be of base curve 1, which allows to test between the infinite and 103 cm.

Example 5: Lens Manufacturing

The lens may be manufactured specifically for the wearer.
By way of example (lens with LOE and POD), the lens is made with the desired base curve, so as to ensure a conjugation between the projection (display) system and the rear face of the lens. This allows comfort visualization for the wearer. Additional information can be found in WO2011/

076604 and US 2010-045927, the content of which is incorporated herein by reference.

The invention claimed is:

1. A method to determine a value of a virtual distance of visualization by a wearer of computer-generated information content displayed by a head-mounted display device, wherein said method comprises the steps of:
   (i) determining a value of comfort amplitude of accommodation of the wearer by first determining a maximal amplitude of accommodation at a punctum proximum defining the closest visible point for the wearer, comprising:
      computing said value of comfort amplitude of accommodation based upon an age of the wearer, or
      performing one or more measurements of said value of comfort amplitude of accommodation, by first providing as a measured distance a maximal amplitude of accommodation at a punctum proximum defining the closest visible point for the wearer;
   (ii) assessing the wearer's accommodative facility under dynamic test conditions, by switching between a visualization of a first display and a visualization of a second display by the same wearer's eye, wherein the second display is situated within the wearer's comfort amplitude of accommodation, comprising:
      (ii-a) setting a first value of visualization distance of the first display;
      (ii-b) setting a second value of visualization distance of the second display situated within the wearer's comfort amplitude of accommodation; and
      (ii-c) assessing the wearer's ability to accommodate during switching for the same wearer's eye between the visualization of the first display situated at a distance having the first value, and the visualization of the second display situated at distance having the second value; and
   (iii) determining a suitable value of the virtual distance based on the results of steps (i) and (ii).

2. The method of claim 1, wherein step (ii) simulates a situation of the wearer switching for the same wearer's eye between a visualization of a virtual display of information content displayed by said head-mounted display device and a visualization of a real object from the wearer environment.

3. The method of claim 1, wherein depending on a switching capacity of the wearer in step (ii), the virtual distance is validated or else changed by repeating steps (ii-a) to (ii-c) so as to reduce the gap between said first value and said second value.

4. The method of claim 1, wherein step (ii-c) further comprises one of a qualitative assessment from the wearer and a quantitative assessment comprising one or more measurements.

5. The method of claim 1, further comprising determining of a virtual amplitude of accommodation for the visualization by the wearer.

6. A method to design a head-mounted display device worn by a wearer and operable to display computer-generated information content and worn by a wearer, wherein the method is based on a determination of a value of a virtual distance of visualization based on the results of the following steps:
   (i) determining a value of comfort amplitude of accommodation of the wearer by first determining a maximal amplitude of accommodation at a punctum proximum defining the closest visible point for the wearer, comprising:
      computing said value of comfort amplitude of accommodation based upon an age of the wearer, or
      performing one or more measurements of said value of comfort amplitude of accommodation, by first providing as a measured distance a maximal amplitude of accommodation at a punctum proximum defining the closest visible point for the wearer; and
   (ii) assessing the wearer's accommodative facility under dynamic test conditions, by switching between a visualization of a first display and a visualization of a second display by the same wearer's eye, wherein the second display is situated within the wearer's comfort amplitude of accommodation, comprising:
      (ii-a) setting a first value of visualization distance of the first display;
      (ii-b) setting a second value of visualization distance of the second display situated within the wearer's comfort amplitude of accommodation; and
      (ii-c) assessing the wearer's ability to accommodate during switching for the same wearer's eye between the visualization of the first display situated at a distance having the first value, and the visualization of the second display situated at distance having the second value; and
   (iii) determining a suitable value of the virtual distance based on the results of steps (i) and (ii).

7. The method of claim 6, wherein the device is a pair of glasses comprising two ophthalmic lenses and wherein one of said ophthalmic lenses comprises a light-guide optical element.

8. The method of claim 7, wherein the lenses are selected from prescription lenses, such as single-vision lenses, multifocal lenses and progressive lenses, and wherein the value of one of the virtual distance and amplitude of accommodation is used to determine one or more optical parameters of the two ophthalmic lenses, the parameters comprising: a value of a base curve, a design of one of a front side and a design of a rear side of an ophthalmic lens of the two ophthalmic lenses.

9. The method of claim 6, further comprising manufacturing the head-mounted display device.

10. The method of claim 9, wherein the method is computer-implemented.

11. A non-transitory computer program product comprising one or more stored sequence(s) of instructions that is accessible to a processor and which, when executed by the processor, causes the processor to perform the steps of:
   (i) determining a value of comfort amplitude of accommodation of the wearer by first determining a maximal amplitude of accommodation at a punctum proximum defining the closest visible point for the wearer, comprising:
      computing said value of comfort amplitude of accommodation based upon an age of the wearer, or
      performing one or more measurements of said value of comfort amplitude of accommodation, by first providing as a measured distance a maximal amplitude of accommodation at a punctum proximum defining the closest visible point for the wearer;
   (ii) assessing the wearer's accommodative facility under dynamic test conditions, by switching between a visualization of a first display and a visualization of a second display by the same wearer's eye, wherein the second display is situated within the wearer's comfort amplitude of accommodation, comprising:
      (ii-a) setting a first value of visualization distance of the first display;

(ii-b) setting a second value of visualization distance of the second display situated within the wearer's comfort amplitude of accommodation; and (ii-c) assessing the wearer's ability to accommodate during switching for the same wearer's eye between the visualization of the first display situated at a distance having the first value, and the visualization of the second display situated at distance having the second value; and (iii) determining a suitable value of the virtual distance based on the results of steps (i) and (ii).

12. The method of claim 1, wherein the method is implemented by a computer.

13. The method of claim 1, wherein in step (i), performing one or more measurements of said value of comfort amplitude of accommodation is carried out according to one of a Push-Up method and a test with an active lens.

14. The method of claim 1, wherein step (ii) comprises utilizing an accommodative rock test with lens flippers.

15. The method of claim 2, where the first value and the second value are selected to simulate the situation.

16. The method of claim 4, wherein the one or more measurements of the quantitative assessment are cyclic measurements.

17. The method of claim 6, wherein determining the value of the virtual distance is performed at least twice, with different gaze directions for at least one of the visualization of the first display and the visualization of the second display.

* * * * *